(12) United States Patent
Cottard et al.

(10) Patent No.: US 7,645,303 B2
(45) Date of Patent: Jan. 12, 2010

(54) COMPOSITION FOR THE OXIDATION DYEING OF HUMAN KERATINOUS FIBRES

(75) Inventors: François Cottard, Levallois-Perret (FR); Christine Rondeau, Sartrouville (FR)

(73) Assignee: L'Oreal S.A., Paris (FR)

( * ) Notice: Subject to any disclaimer, the term of this patent is extended or adjusted under 35 U.S.C. 154(b) by 60 days.

(21) Appl. No.: 10/510,629

(22) PCT Filed: Apr. 11, 2003

(86) PCT No.: PCT/EP03/04697

§ 371 (c)(1), (2), (4) Date: Jun. 6, 2005

(87) PCT Pub. No.: WO03/084495

PCT Pub. Date: Oct. 16, 2003

(65) Prior Publication Data

US 2005/0229330 A1 Oct. 20, 2005

Related U.S. Application Data

(60) Provisional application No. 60/372,454, filed on Apr. 16, 2002.

(30) Foreign Application Priority Data

Apr. 11, 2002 (FR) .................................. 02 04525

(51) Int. Cl.
*A61Q 5/10* (2006.01)

(52) U.S. Cl. ...................... 8/405; 8/406; 8/410; 8/421; 8/435; 8/581; 8/619

(58) Field of Classification Search ............. 8/405, 8/406, 410, 421, 435, 581, 619
See application file for complete search history.

(56) References Cited

U.S. PATENT DOCUMENTS

| 5,053,051 | A | 10/1991 | Tennigkeit et al. |
| 5,061,289 | A | 10/1991 | Clausen et al. |
| 5,380,340 | A | 1/1995 | Neunhoeffer et al. |
| 5,534,267 | A | 7/1996 | Neunhoeffer et al. |
| 5,766,576 | A | 6/1998 | Lowe et al. |
| 6,099,592 | A | 8/2000 | Vidal et al. |
| 6,099,593 | A | 8/2000 | Terranova et al. |
| 6,206,935 | B1 | 3/2001 | Onitsuka et al. |
| 6,284,003 | B1 | 9/2001 | Rose et al. |
| 6,383,232 | B1 | 5/2002 | Wohlman et al. |
| 6,669,933 | B2 * | 12/2003 | Duffer et al. ............... 424/70.1 |

FOREIGN PATENT DOCUMENTS

| DE | 23 59 399 | 6/1975 |
| DE | 38 43 892 | 6/1990 |
| DE | 41 33 957 | 4/1993 |
| DE | 195 43 988 | 5/1997 |
| EP | 0 148 466 | 7/1985 |
| EP | 0 362 302 | 4/1990 |
| FR | 2 750 048 | 6/1996 |
| FR | 2 733 749 | 11/1996 |
| GB | 1 026 978 | 4/1966 |
| GB | 1 153 196 | 6/1966 |
| JP | 60-155108 | 8/1985 |
| JP | 01-165514 | 6/1989 |
| JP | 2-019576 | 1/1990 |
| JP | 9-110659 | 4/1997 |
| JP | 2000-247850 | 9/2000 |
| JP | 2001-328926 | 11/2001 |
| JP | 2002-097120 | 4/2002 |
| JP | 2002-308744 | 10/2002 |
| WO | WO 94/08969 | 4/1994 |
| WO | WO 94/08970 | 4/1994 |
| WO | WO 96/15765 | 5/1996 |

OTHER PUBLICATIONS

English Language Derwent Abstract for DE 23 59 399.
English Language Derwent Abstract for JP 2-019576.
English Language Derwent Abstract for JP 9-110659.
English language Patent Abstract of JP 2001-328926, Nov. 27, 2001.
English language Patent Abstract of JP 01-165514, Jun. 29, 1989.
English language Patent Abstract of JP 2002-097120, Apr. 2, 2002.
English Language Abstract for JP-2002-308744, (2002).

* cited by examiner

*Primary Examiner*—Eisa B Elhilo
(74) *Attorney, Agent, or Firm*—Finnegan, Henderson, Farabow, Garrett & Dunner, LLP

(57) ABSTRACT

The subject of the invention is a composition for the oxidation dyeing of human keratinous fibers and in particular hair comprising, in a cosmetically acceptable medium based on water and at a basic pH, at least one oxidation dye and an alkalinizing agent consisting of sodium metasilicate and aqueous ammonia, and the dyeing method using this composition.

33 Claims, No Drawings

COMPOSITION FOR THE OXIDATION DYEING OF HUMAN KERATINOUS FIBRES

This application is a national stage application from international application no. PCT/EP03104697, filed Apr. 11, 2003, which claims benefit of 60/372,454, filed on Apr. 16, 2002, which claims priority to French Application No. FR 02/04525, filed on Apr. 11, 2002, all of which are herein incorporated by reference.

The subject of the invention is a composition for the oxidation dyeing of human keratinous fibres and in particular hair comprising, in a cosmetically acceptable medium based on water and at a basic pH, at least one oxidation dye and an alkalinizing agent consisting of sodium metasilicate and aqueous ammonia, and the dyeing method using this composition.

It is known to dye human keratinous fibres and in particular hair with dyeing compositions containing oxidation dyes. Oxidation dyes comprise oxidation dye precursors and couplers. Oxidation dye precursors, generally called oxidation bases, are colourless or weakly coloured compounds which, combined with oxidizing products, can give rise to coloured and dye compounds by a process of oxidative condensation. They are in particular ortho- or para-phenylene diamines ortho- or para-aminophenols, or heterocyclic bases.

The shades obtained with these oxidation bases may be modified by combining the said bases with couplers or colour modifiers, the couplers being chosen in particular from aromatic meta-diamines, meta-aminophenols, meta-diphenols and certain heterocyclic compounds.

The variety of molecules used in oxidation bases and couplers allows a rich palette of colours to be obtained.

The oxidation dyeing method consists in applying to the fibres oxidation bases or a mixture of oxidation bases and couplers with an oxidizing agent, most often hydrogen peroxide, in allowing to act, and then in rinsing the fibres. The application, which is generally carried out at a basic pH, makes it possible to obtain dyeing and simultaneously lightening of the fibre, which results in practice in the possibility of obtaining a final coloration which is lighter than the original colour. In addition, the lightening of the fibre has the advantageous effect of generating a uniform colour in the case of grey hair, and in the case of naturally pigmented hair, of making the colour stand out, that is to say of making it more visible.

The lightening of hair is evaluated by the tone height which characterizes the degree or level of lightening. The notion of "tone" is based on the classification of natural shades, a tone separating each shade from the one immediately following it or preceding it. This definition and the classification of natural shades is well known to hair styling professionals and is published in the book "Sciences des traitements capillaires" [Science of hair treatment] by Charles ZVIAK, 1988, Ed. Masson, pp. 215 and 278.

The tone heights range from 1 (black) to 10 (light blonde), one unit corresponding to one tone; the higher the figure, the lighter the shade.

As current lightening oxidation dyeing technology has to make it possible to obtain a lightening of the fibre of 2 tones to 2 and a half tones, and a covering of hair which is 100% white, it has up until now involved using aqueous ammonia as alkalinizing agent in high concentrations.

However, as everyone knows, aqueous ammonia has the major disadvantage or releasing a very irritant and unpleasant odour during application of the dye. It also sometimes causes, in high concentrations, irritations of the scalp in the form of pricklings.

Now, after major research studies carried out on the subject, the applicant has just discovered that it is possible to reduce the irritating odour and the risks of scalp irritation of the said dyes while obtaining acceptable lightening levels and intense colorations in varied shades, using, as alkalinizing agent, a mixture of sodium metasilicate and aqueous ammonia.

This discovery forms the basis of the present invention.

The first subject of the invention is therefore a dyeing composition for the oxidation dyeing of human keratinous fibres and more particularly hair, free of oxidizing agent, comprising, in a cosmetically acceptable medium based on water and at a basic pH, at least one oxidation dye and an alkalinizing agent, characterized in that the alkalinizing agent is a combination of sodium metasilicate and aqueous ammonia.

The expression "dyeing composition" is understood to mean, for the purposes of the invention, a composition comprising at least one oxidation dye, which has to be in the presence of an oxidizing agent during use.

The dyeing composition in accordance with the invention makes it possible to reduce the amount of aqueous ammonia conventionally used while the dyeing properties are perfectly maintained and makes it possible to formulate less odorous and less irritating products.

The subject of the invention is also a method for the oxidation dyeing of human keratinous fibres and more particularly hair using the said dyeing composition. The method consists in mixing, at the time of use, a dyeing composition comprising 0.4 to 1.3% by weight of ammonia relative to the total weight of the dyeing composition, with an oxidizing composition comprising hydrogen peroxide or a compound capable of releasing hydrogen peroxide in situ, or an oxidoreduction enzyme; the amount of the oxidizing composition being at most 6 times the amount of the dyeing composition; the mixture obtained is then applied to the fibres, is allowed to act, after which the fibres are rinsed, optionally washed with shampoo and rinsed again, and dried.

The invention is also relating to a method for the oxidation dyeing of human keratinous fibres and more particularly hair using the said dyeing composition. The method consists in mixing, at the time of use, a dyeing composition comprising 1 to 3% by weight of sodium metasilicate, relative to the total weight of the dyeing composition, with an oxidizing composition comprising hydrogen peroxide or a compound capable of releasing hydrogen peroxide in situ, or an oxidoreduction enzyme; the amount of the oxidizing composition being at at least the amount of the dyeing composition; the mixture obtained is then applied to the fibres, is allowed to act, after which the fibres are rinsed, optionally washed with shampoo and rinsed again, and dried.

Another subject of the invention is a ready-to-use composition for the oxidation dyeing of human keratinous fibres, and more particularly hair comprising the mixture of a dyeing composition described above, comprising 0.4 to 1.3% by weight of ammonia, relative to the total weight of the dyeing composition, and an oxidizing composition; the amount of the oxidizing composition being at most 6 times the amount of the dyeing composition.

Another subject of the invention is a ready-to-use composition for the oxidation dyeing of human keratinous fibres, and more particularly hair comprising the mixture of a dyeing composition described above, comprising 1 to 3% by weight of sodium metasilicate, relative to the total weight of the dyeing composition, and an oxidizing composition; the amount of the oxidizing composition being at least the amount of the dyeing composition.

The expression "ready-to-use composition" is understood to mean, for the purposes of the invention, the composition intended to be applied as it is to keratinous fibres, that is to say that it can be stored as it is before use or can result from mixing two compositions immediately before use.

Alkalinizing Agent

The combination according to the invention of sodium metasilicate and aqueous ammonia used as alkalinizing agent should make it possible to adjust the pH of the dyeing composition of the present invention at a basic pH, more particularly at a pH from 7.5 to 13, and preferably from 8.5 to 11.5.

According to the present invention, the said combination comprises, as active substance, more particularly at least 0.1% by weight, preferably at least 0.5% by weight, and more preferably at least 0.1% by weight of sodium metasilicate, relative to the total weight of the dyeing composition.

Moreover, the amount of sodium metasilicate in the combination is advantageously of at most 6% by weight, more particularly of at most 5% by weight, and preferably of at most 3% by weight, relative to the total weight of the dyeing composition.

More particularly, the said combination comprises, as active substance, from 0.1 to 6% by weight approximately of sodium metasilicate, preferably from 0.5 to 5%, and more particularly from 1 to 3% relative to the total weight of the dyeing composition.

According to the present invention, the said combination comprises, as active substance, more particularly at least 0.1% by weight, preferably at least 0.4% by weight, and more preferably at least 0.6% by weight of ammonia, relative to the total weight of the dyeing composition.

Moreover, the amount of ammonia in the combination is more especially of at most 1.6% by weight, preferably of at most 1.3% by weight, more preferably of at most 1.2% by weight, and more particularly of at most 1% by weight, relative to the total weight of the dyeing composition.

More particularly, the combination comprises from 0.1 to 1.6% by weight approximately of ammonia, preferably from 0.4 to 1.3% by weight, more particularly from 0.4 to 1.2% by weight, and more preferably from 0.6 to 1% by weight, relative to the total weight of the dyeing composition.

It has to be mentioned that according to one advantageous embodiment of the invention, the weight ratio of ammonia to sodium metasilicate is comprised between 0.02 and 15, more particularly between 0.1 and 5, preferably between 0.3 and 2, and more preferably between 0.4 and 1.

According to the present invention, sodium metasilicate [$Na_2SiO_3$] is an anhydrous compound, but it can also exist in its hydrated forms with 5 or 9 molecules of water. Ammonia is introduced into the formulae in the form of aqueous ammonia, which is an aqueous solution of ammonia. The aqueous ammonia generally used has a titre of 20 to 25% by weight of ammonia.

The present invention makes it possible to reduce the amount of aqueous ammonia on the basis of an aqueous solution having a titre of 20.5% ammonia, from 20 to 80% and more particularly from 30 to 60%.

Medium

The cosmetically acceptable medium for dyeing in accordance with the invention consists of water or of a mixture of water and at least one organic solvent for solubilizing the compounds which might not be sufficiently soluble in water. As organic solvent, there may be mentioned, for example, $C_1$-$C_4$ alkanols, such as ethanol and isopropanol; glycerol; glycols and glycol ethers such as 2-butoxyethanol, propylene glycol, monomethyl ether of propylene glycol, monoethyl ether and monomethyl ether of diethylene glycol, and aromatic alcohols such as benzyl alcohol or phenoxyethanol, analogous products and mixtures thereof.

The solvents may be present in proportions preferably ranging from 1 to 40% by weight approximately relative to the total weight of the dyeing composition, and still more preferably from 5 to 30% by weight approximately.

Oxidation Dyes

The oxidation dyes which can be used according to the invention are chosen from oxidation bases and/or couplers.

Preferably, the compositions according to the invention contain at least one oxidation base.

The oxidation bases are chosen from those conventionally known in oxidation dyeing, and among which there may be mentioned in particular ortho- and para-phenylenediamines, double bases, ortho- and para-aminophenols, the following heterocyclic bases and their addition salts with an acid.

There may be mentioned in particular:

(I) the para-phenylenediamines of the following formula (I) and their addition salts with an acid:

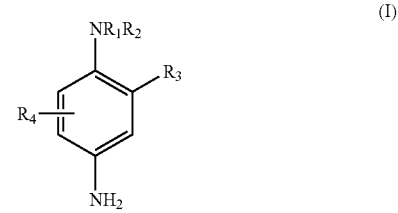

in which:

$R_1$ represents a hydrogen atom, a $C_1$-$C_4$ alkyl radical, a monohydroxy($C_1$-$C_4$ alkyl) radical, a polyhydroxy-($C_2$-$C_4$ alkyl) radical, a ($C_1$-$C_4$)alkoxy($C_1$-$C_4$)alkyl radical, a $C_1$-$C_4$ alkyl radical substituted with a nitrogen-containing group, a phenyl radical or a 4'-aminophenyl radical;

$R_2$ represents a hydrogen atom, a $C_1$-$C_4$ alkyl radical, a monohydroxy($C_1$-$C_4$ alkyl) radical, a polyhydroxy($C_2$-$C_4$ alkyl) radical a with radical or a $C_1$-$C_4$ alkyl radical substituted with a nitrogen-containing group;

$R_1$ and $R_2$ may also form with the nitrogen atom carrying them a 5- or 6-membered nitrogen-containing heterocycle optionally substituted with one or more alkyl, hydroxyl or ureido groups;

$R_3$ represents a hydrogen atom, a halogen atom such as a chlorine atom, a $C_1$-$C_4$ alkyl radical, a sulpho radical, a carboxyl radical, a monohydroxy($C_1$-$C_4$ alkyl) radical, a hydroxy($C_1$-$C_4$ alkoxy) radical, an acetylamino($C_1$-$C_4$ alkoxy) radical, a mesylamino($C_1$-$C_4$ alkoxy) radical or a carbamoylamino($C_1$-$C_4$ alkoxy) radical, $R_4$ represents a hydrogen or halogen atom or a $C_1$-$C_4$ alkyl radical.

Among the nitrogen-containing groups of formula (I) above, there may be mentioned in particular the amino, mono ($C_1$-$C_4$)alkylamino, ($C_1$-$C_4$)dialkylamino, ($C_1$-$C_4$)trialkylamino, monohydroxy($C_1$-$C_4$)alkylamino, imidazolinium and ammonium radicals.

Among the para-phenylenediamines of formula (I) above, there may be mentioned more particularly para-phenylenediamine, para-tolylenediamine, 2-chloro-paraphenylene-diamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-paraphenylenediamine, N,N-dipropyl-para-phenylenediamine, 4-amino-N,N-diethyl-3-methylaniline, N,N-bis(β-hydroxyethyl)-para-phenylenediamine, 4-N,N-bis(5-hydroxyethyl) amino-2-methylaniline, 4-N,N-bis(5-hydroxy-ethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N,N-(ethyl-β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-O-hydroxyethyloxy-para-phenylenediamine, 2-A-acetylamino-ethyloxy-para-phenylenediamine, N-(β-methoxyethyl)-para-phenylenediamine, 2-methyl-1-N-5-hydroxyethyl-para-phenylenediamine, N-(4-aminophenyl)-3-hydroxypyrrolidine, and their addition salts with an acid.

Among the para-phenylenediamines of formula (I) above, there are most particularly preferred para-phenylenediamine, para-tolylenediamine, 2-isopropyl-paraphenylene-diamine, 2-β-hydroxyethyl-para-phenylenediamine, 2-β-hydroxyethyloxy-para-phenylene-diamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine, and their addition salts with an acid.

(II) According to the invention, "double bases" is understood to mean the compounds containing at least two aromatic rings on which amino and/or hydroxyl groups are carried.

Among the double bases which can be used as oxidation bases in the dyeing compositions in accordance with the invention, there may be mentioned in particular the compounds corresponding to the following formula (II), and their addition salts with an acid:

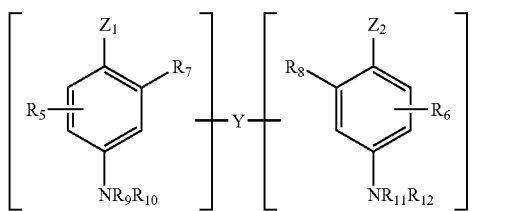

in which:
Z$_1$ and Z$_2$, which are identical or different, represent a hydroxyl or —NH$_2$ radical which may be substituted with a C$_1$-C$_4$ alkyl radical or with a linking arm Y;
the linking arm Y represents a linear or branched alkylene chain comprising from 1 to 14 carbon atoms, which may be interrupted by or which may end with one or more nitrogen-containing groups and/or one or more heteroatoms such as oxygen, sulphur or nitrogen atoms, and optionally substituted with one or more hydroxyl or C$_1$-C$_6$ alkoxy radicals;
R$_5$ and R$_6$ represent a hydrogen or halogen atom, a C$_1$-C$_4$ alkyl radical, a monohydroxy(C$_1$-C$_4$ alkyl) radical, a polyhydroxy(C$_2$-C$_4$ alkyl) radical, an amino(C$_1$-C$_4$ alkyl) radical or a linking arm Y;
R$_7$, R$_8$, R$_9$, R$_{10}$, R$_{11}$ and R$_{12}$, which are identical or different, represent a hydrogen atom, a linking arm Y or a C$_1$-C$_4$ alkyl radical;

it being understood that the compounds of formula (II) contain only one linking arm Y per molecule.

Among the nitrogen-containing groups of formula (II) above, there may be mentioned in particular the amino, mono (C$_1$-C$_4$)alkylamino, (C$_1$-C$_4$)dialkylamino, (C$_1$-C$_4$)trialkylamino, monohydroxy(C$_1$-C$_4$)alkylamino, imidazolinium and ammonium radicals.

Among the double bases of formulae (II) above, there may be mentioned more particularly N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)-tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl) ethylene-diamine, 1,8-bis(2,5-diaminophenoxy)-3,5-dioxaoctane, and their addition salts with an acid.

Among these double bases of formula (II), N,N'-bis(β-hydroxyethyl)-N,N'-bis(4'-aminophenyl)-1,3-diaminopropanol, 1,8-bis(2,5-diaminophenoxy)-3,5-dioxaoctane or one of their addition salts with an acid are particularly preferred.

(III) The para-aminophenols corresponding to the following formula (III), and their addition salts with an acid:

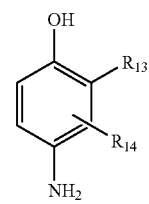

in which:
R$_{13}$ represents a hydrogen atom, or a halogen atom such as fluorine, a C$_1$-C$_4$ alkyl, monohydroxy(C$_1$-C$_4$ alkyl), (C$_1$-C$_4$)alkoxy(C$_1$-C$_4$)-alkyl, amino(C$_1$-C$_4$ alkyl) or hydroxy(C$_1$-C$_4$)alkylamino-(C$_1$-C$_4$ alkyl) radical,
R$_{14}$ represents a hydrogen atom, or a halogen atom such as fluorine, a C$_1$-C$_4$ alkyl, monohydroxy(C$_1$-C$_4$ alkyl), polyhydroxy(C$_2$-C$_4$ alkyl), amino(C$_1$-C$_4$ alkyl), cyano (C$_1$-C$_4$ alkyl) or (C$_1$-C$_4$)alkoxy(C$_1$-C$_4$)alkyl radical.

Among the para-aminophenols of formula (III) above, there may be mentioned more particularly para-aminophenol, 4-amino-3-methylphenol, 4-amino-3-fluorophenol, 4 amino-3-hydroxymethylphenol, 4-amino-2-methylphenol, 4-amino-2-hydroxymethyl-phenol, 4-amino-2-methoxymethylphenol, 4-amino-2-aminomethylphenol, 4-amino-2-(β-hydroxyethylaminomethyl)phenol, and their addition salts with an acid.

(IV) The ortho-aminophenols which can be used as oxidation bases in the context of the present invention are chosen in particular from 2-aminophenol, 2-amino-1-hydroxy-5-methylbenzene, 2-amino-1-hydroxy-6-methylbenzene, 5-acetamido-2-aminophenol, and their addition salts with acid.

(V) Among the heterocyclic bases which can be used as oxidation bases in the dyeing compositions in accordance with the invention, there may be mentioned more particularly pyridine derivatives, pyrimidine derivatives, pyrazole derivatives, and their addition salts with an acid.

Among the pyridine derivatives, there may be mentioned more particularly the compounds described for example in Patents GB 1,026,978 and GB 1,153,196, such as 2,5-diaminopyridine, 2-(4-methoxyphenyl)amino-3-aminopyridine, 2,3-diamino-6-methoxypyridine, 2-(β-methoxyethyl)amino-3-amino-6-methoxypyridine, 3,4-diamino-pyridine, and their addition salts with an acid.

Among the pyrimidine derivatives, there may be mentioned more particularly the compounds described, for example, in Patents DE 2,359,399; JP 88-169 571; JP 91-10659 or Patent Application WO 96/15765, such as 2,4,5,6-tetraminopyrimidine, 4-hydroxy-2,5,6-triaminopyrimidine, 2-hydroxy-4,5,6-triaminopyrimidine, 2,4-dihydroxy-5,6-diaminopyrimidine, 2,5,6-triamino-pyrimidine, and the pyrazolopyrimidine derivatives such as those mentioned in Patent Application FR-A-2 750 048 and among which there may be mentioned pyrazolo[1,5-a]-pyrimidine-3,7-diamine; 2,5-dimethyl-pyrazolo[1,5-a]-pyrimidine-3,7-diamine; pyrazolo[1,5-a]pyrimidine-3,5-diamine; 2,7-dimethylpyrazolo[1,5-a]pyrimidine-3,5-diamine; 3-aminopyrazolo[1,5-a]pyrimidin-7-ol; 3-amino-pyrazolo[1,5-a]pyrimidin-5-ol; 2-(3-amino-pyrazolo-[1,5-a]pyrimidin-7-ylamino)ethanol, 2-(7-amino-pyrazolo[1,5-a]pyrimidin-3-ylamino)ethanol, 2-[(3-amino-pyrazolo[1,5-a]pyrimidin-7-yl)-(2-hydroxyethyl)amino]-ethanol, 2-[(7-aminopyrazolo[1,5-a]-pyrimidin-3-yl)-(2-hydroxyethyl) amino]ethanol, 5,6-dimethylpyrazolo-[1,5-a]pyrimidine-3,7-diamine, 2,6-dimethyl-pyrazolo-[1,5-a]pyrimidine-3,7-diamine, 2,5,N7,N7-tetramethyl-pyrazolo[1,5-a]pyrimidine-3,7-diamine, 3-amino-5-methyl-7-imidazolylpropyl-aminopyrazolo[1,5-a]-pyrimidine, their addition salts and their tautomeric forms, when a tautomeric equilibrium exists and their addition salts with an acid.

Among the pyrazole derivatives, there may be mentioned more particularly the compounds described in Patents DE 3,843,892, DE 4 133 957 and Patent Applications WO 94/08969, WO 94/08970, FR-A-2 733 749 and DE 195 43 988 such as 4,5-diamino-1-methylpyrazole, 3,4-diaminopyrazole, 4,5-diamino-1-(4'-chlorobenzyl)-pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazino-pyrazole, 1-benzyl-4,5-diamino-3-methyl-pyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-(β-hydroxyethyl)pyrazole, 4,5-diamino-1-ethyl-3-methylpyrazole, 4,5-diamino-1-ethyl-3-(4'-methoxyphenyl) pyrazole, 4,5-diamino-1-ethyl-3-hydroxy-methylpyrazole, 4,5-diamino-3-hydroxymethyl-1-methylpyrazole, 4,5-diamino-3-hydroxymethyl-1-isopropyl-pyrazole, 4,5-diamino-3-methyl-1-isopropyl-pyrazole, 4-amino-5-(2'-aminoethyl)amino-1,3-dimethyl-pyrazole, 3,4,5-triaminopyrazole, 1-methyl-3,4,5-triamino-pyrazole, 3,5-diamino-1-methyl-4-methylaminopyrazole, 3,5-diamino-4-(O-hydroxy-ethyl)amino-1-methylpyrazole, and their addition salts with an acid.

According to the present invention, the oxidation bases preferably represent from 0.0005 to 12% by weight approximately of the total weight of the composition, and still more preferably from 0.005 to 8% by weight approximately of this weight.

The couplers which can be used in the dyeing composition according to the invention are those conventionally used in oxidation dyeing compositions, that is to say meta-aminophenols, meta-phenylenediamines, meta-diphenols, naphthols and heterocyclic couplers such as, for example, indole derivatives, indoline derivatives, sesamol and its derivatives, pyridine derivatives, pyrazolotriazole derivatives, pyrazolones, indazoles, benzimidazoles, benzothiazoles, benzoxazoles, 1,3-benzodioxoles, quinolines and their addition salts with an acid.

These couplers are more particularly chosen from 2,4-diamino-1-(O-hydroxyethyloxy)benzene, 2-methyl-5-aminophenol, 5-N-(β-hydroxyethyl)amino-2-methylphenol, 3-aminophenol, 2-chloro-3-amino-6-methylphenol, 1,3-dihydroxybenzene, 1,3-dihydroxy-2-methylbenzene, 4-chloro-1,3-dihydroxybenzene, 2-amino-4-(β-hydroxy ethylamino)-1-methoxybenzene, 1,3-diaminobenzene, 1,3-bis(2,4-diaminophenoxy)-propane, sesamol, 1-amino-2-methoxy-4,5-methylene-dioxybenzene, α-naphthol, 6-hydroxyindole, 4-hydroxyindole, 4-hydroxy-N-methylindole, 6-hydroxy-indoline, 2,6-dihydroxy-4-methylpyridine, 1-H-3-methylpyrazol-5-one, 1-phenyl-3-methylpyrazol-5-one, 2-amino-3-hydroxypyridine, 3,6-dimethyl-pyrazolo[3,2-c]-1,2,4-triazole, 2,6-dimethyl-pyrazolo[1,5-b]-1,2,4-triazole and their addition salts with an acid.

When they are present, these couplers preferably represent from 0.0001 to 10% by weight approximately of the total weight of the composition, and still more preferably from 0.005 to 5% by weight approximately.

In general, the addition salts with an acid of the oxidation bases and couplers are chosen in particular from the hydrochlorides, hydrobromides, sulphates, tartrates, lactates and acetates.

The composition according to the invention may also contain, in addition to the oxidation dyes defined above, direct dyes for enriching the shades with glints. These direct dyes may then be chosen in particular from neutral, cationic or anionic nitro, azo or anthraquinone dyes in the proportion by weight of about 0.001 to 20%, and preferably 0.01 to 10% of the total weight of the composition.

Adjuvants

The dyeing composition in accordance with the invention may also contain various adjuvants which are conventionally used in hair dyeing compositions, such as anionic, cationic, nonionic, amphoteric or zwitterionic surfactants or mixtures thereof, fatty alcohols, fatty acids, anionic, cationic, nonionic, amphoteric or zwitterionic polymers or mixtures thereof, inorganic or organic thickening agents or thickening polymers such as, for example, nonionic guar gums, associative polymers containing at least one hydrophilic unit and at least one fatty chain and of a nonionic, anionic, cationic or amphoteric nature, antioxidants or reducing agents, penetrating agents, sequestering agents such as EDTA and etidronic acid, UV-screening agents, waxes, perfumes, buffers, dispersing agents, conditioning agents such as, for example, modified or unmodified, volatile or nonvolatile silicones, film-forming agents, pearlescent agents, preservatives, ceramides, pseudoceramides, vegetable, mineral or synthetic oils, vitamins or provitamins such as panthenol, opacifiers, and the like.

Preferably, the dyeing composition of the invention contains at least one cationic polymer in the proportion of about 0.05 to 10% by weight, and at least one surfactant, which is preferably nonionic, in the proportion of 0.1 to 20% by weight.

Preferably, it also contains at least one thickening polymer preferably chosen from associative polymers in the proportion of about 0.05 to 10% by weight.

The reducing agents or antioxidants may be chosen in particular from sodium sulphite, thioglycolic acid and thiolactic acid and their salts of ammonium, sodium bisulphite, dehydroascorbic acid, hydroquinone, 2-methylhydroquinone, tert-butylhydroquinone, homogentisic acid, and they are then generally present in quantities ranging from about 0.05 to 3% by weight relative to the total weight of the composition.

Of course, persons skilled in the art will be careful to choose this or these possible additional compounds such that the advantageous properties intrinsically attached to the dyeing composition in accordance with the invention are not, or not substantially, impaired by the addition(s) envisaged.

According to a first embodiment, the dyeing method according to the invention comprises the following steps: there are mixed, at the time of use, a dyeing composition as described above and in particular comprising, in a cosmetically acceptable medium based on water and at a basic pH, at least one oxidation dye and a combination of sodium metasilicate and aqueous ammonia, the amount of ammonia being from 0.4 to 1.3% by weight relative to the total weight of the dyeing composition, with an oxidizing composition; the amount of the oxidizing composition being at most 6 times the weight of the dyeing composition, the mixture obtained is then applied to the keratinous fibres, it is allowed to act, after which the keratinous fibres are rinsed, optionally washed with shampoo and rinsed again, then dried.

According to a particular embodiment of the invention, the weight ratio dyeing composition/oxidizing composition is comprised between 2/1 and 1/6, and preferably between 1/1 and 1/3.

According to a second embodiment, the dyeing method according to the invention comprises the following steps: there are mixed, at the time of use, a dyeing composition as described above and in particular comprising, in a cosmetically acceptable medium based on water and at a basic pH, at least one oxidation dye and a combination of sodium metasilicate and aqueous ammonia, the amount of sodium metasilicate being from 1 to 3% by weight relative to the total weight of the dyeing composition, with an oxidizing composition; the amount of the oxidizing composition being at least the weight of the dyeing composition, the mixture obtained is then applied to the keratinous fibres, it is allowed to act, after which the keratinous fibres are rinsed, optionally washed with shampoo and rinsed again, then dried.

According to a particular embodiment of the invention, the weight ratio dyeing composition/oxidizing composition is comprised between 1/1 and 1/6, and preferably between 1/1 and 1/3.

The pH of the composition is ranging more particularly from 7.5 to 13.

Moreover, the said mixture is advantageously allowed to act for 3 to 50 minutes approximately, preferably 5 to 30 minutes approximately.

The dyeing composition, before mixing with the oxidant, may be in various forms, such as a liquid, cream or gel form, optionally pressurized or in any other form appropriate for carrying out, after mixing, a dyeing of human keratinous fibres and in particular hair.

Oxidant

In the oxidizing composition, the oxidizing agent is chosen from hydrogen peroxide and compounds capable of releasing hydrogen peroxide in situ, oxidoreduction enzymes such as laccases, peroxidases and oxidoreductases containing 2 electrons (such as uricase), where appropriate in the presence of their respective donor or cofactor.

The use of hydrogen peroxide is particularly preferred. This oxidizing agent advantageously consists of a solution of hydrogen peroxide whose titre may vary, more particularly, from about 1 to 40 volumes, and still more preferably from about 5 to 40.

According to a first embodiment of the invention, the ready-to-use composition for the oxidation dyeing of human keratinous fibres, and more particularly hair comprising the mixture of a dyeing composition described above, comprising 0.4 to 1.3% by weight of ammonia, relative to the total weight of the dyeing composition, with an oxidizing composition; the amount of the oxidizing composition being at most 6 times the amount of the dyeing composition.

More especially, the weight ratio dyeing composition/oxidizing composition is comprised between 2/1 and 1/6, and preferably between 1/1 and 1/3.

A second embodiment consists in a ready-to-use composition for the oxidation dyeing of human keratinous fibres, and more particularly hair comprising the mixture of a dyeing composition described above, comprising 1 to 3% by weight of sodium metasilicate, relative to the total weight of the dyeing composition, with an oxidizing composition; the amount of the oxidizing composition being at least the amount of the dyeing composition.

More especially, the weight ratio dyeing composition/oxidizing composition is comprised between 1/1 and 1/6, and preferably between 1/1 and 1/3.

The examples which follow are intended to illustrate the invention without, however, exhibiting a limiting character.

EXAMPLES 1-3

The following dyeing compositions were prepared:

(amounts expressed in grams of active substance)

|  | Example 1 | Example 2 | Example 3 |
| --- | --- | --- | --- |
| Para-phenylenediamine . . . | 0.24 | 0.24 | 0.24 |
| Para-aminophenol . . . | 0.44 | 0.44 | 0.44 |
| 2-aminophenol . . . | 0.028 | 0.028 | 0.028 |
| 1,3-dihydroxybenzene . . . | 0.192 | 0.192 | 0.192 |
| 3-aminophenol . . . | 0.019 | 0.019 | 0.019 |
| 5-N-(β-hydroxyethyl)amino-2-methylphenol . . . | 0.021 | 0.021 | 0.021 |
| 1,3-dihydroxy-2-methylbenzene . . . | 0.055 | 0.055 | 0.055 |
| Anhydrous sodium metasilicate . . . | 2 | 2 | 2 |
| Ammonia (Aqueous ammonia containing 20.5% Wt of $NH_3$) . . . | 1.23 | 1.23 | 1.23 |
| Reducing agent, antioxidant, sequestrant, perfume . . . | q.s. | q.s. | q.s. |
| Propylene glycol . . . | 10 | 10 | 10 |
| Anionic polymer: crosslinked polyacrylic acid. | 0.4 | 0.4 | 0.4 |
| Amphoteric polymer: polyquaternium 22 | 1.5 | 1.5 |  |

-continued

| | Example 1 | Example 2 | Example 3 |
|---|---|---|---|
| (C.T.F.A. name) Merquat 280 sold by the company CALGON ... | | | |
| Cationic polymer: polyquaternium 6 (C.T.F.A name) Merquat 100 sold by the company MERCK ... | | | 2.8 |
| Cationic polymer: Hexadimethrine Chloride (C.T.F.A. name) Mexomer PO sold by the company CHIMEX ... | 3 | 3 | |
| Anionic surfactant: powdered sodium lauryl sulphate ... | 3 | | |
| Nonionic surfactant: oxyethylenated lauryl alcohol containing 12 mol of ethylene oxide ... | | 7.5 | 7.5 |
| Nonionic surfactant: oxyethylenated oleocetyl alcohol containing 30 mol of ethylene oxide ... | | 4 | 4 |
| Nonionic surfactant: oxyethylenated decyl alcohol containing 3 mol of ethylene oxide ... | 10 | 10 | 10 |
| Nonionic surfactant: oxyethylenated decyl alcohol containing 5 mol of ethylene oxide ... | 8 | | |
| Lauric acid ... | | 2.5 | 2.5 |
| Cetylstearyl alcohol 50/50 ... | | 11.5 | 11.5 |
| Pearlescent agent: hydrophobic pyrogenic silica ... | | 1.2 | 1.2 |
| Pearlescent agent: glyceryl monostearate ... | | 2 | 2 |
| Demineralized water ... qs ... | | 100 | 100 |

At the time of use, each dyeing composition described above is mixed weight for weight with a solution of hydrogen peroxide at 20 volumes (6% by weight).

The mixtures thus prepared were applied for 30 minutes to locks of natural or permanently waved grey hair which is 90% white. The locks were then rinsed, washed with a standard shampoo, rinsed again and then dried.

It was observed that these mixtures were a lot less odorous than those of the prior art with satisfactory application qualities.

The hair was dyed in a strong shade of golden blonde colour for each of Examples 1 to 3.

Compared with prior art compositions which are identical except that they do not contain sodium metasilicate and have a much higher content of ammonia of about 2% as active substance, the dyeing performances of compositions 1 to 3 were preserved.

The invention claimed is:

1. A dyeing composition for the oxidation dyeing of human keratinous fibers, wherein the dyeing composition is free of oxidizing agents and comprises, in a cosmetically acceptable medium based on water and at a basic pH, at least one oxidation dye and at least one alkalinizing agent, said at least one alkalinizing agent comprising a combination of aqueous ammonia and from 1% to 3% by weight of sodium metasilicate relative to the total weight of the dyeing composition, and said at least one alkalinizing agent comprising, as an active substance, at most 1.6% by weight of ammonia relative to the total weight of the dyeing composition.

2. A dyeing composition according to claim 1, wherein said human keratinous fibers are hair.

3. A dyeing composition according to claim 1, wherein the at least one alkalinizing agent comprises, as an active substance, at least 0.1% by weight of ammonia relative to the total weight of the dyeing composition.

4. A dyeing composition according to claim 3, wherein the at least one alkalinizing agent comprises, as an active substance, at least 0.6% by weight of ammonia relative to the total weight of the dyeing composition.

5. A dyeing composition according to claim 1, wherein the at least one alkalinizing agent comprises, as an active substance, at most 1% by weight of ammonia relative to the total weight of the dyeing composition.

6. A dyeing composition according to claim 3, wherein the at least one alkalinizing agent comprises, as an active substance, from 0.4% to 1.2% by weight of ammonia relative to the total weight of the dyeing composition.

7. A dyeing composition according to claim 6, wherein the at least one alkalinizing agent comprises, as an active substance, from 0.6% to 1% by weight of ammonia relative to the total weight of the dyeing composition.

8. A dyeing composition according to claim 1, wherein pH of the composition ranges from 7.5 to 13.

9. A dyeing composition according to claim 8, wherein pH of the composition ranges from 8.5 to 11.5.

10. A dyeing composition according to claim 1, wherein the at least one oxidation dye is chosen from oxidation bases and couplers and the acid addition salts thereof.

11. A dyeing composition according to claim 10, comprising at least one oxidation base.

12. A dyeing composition according to claim 11, wherein the at least one oxidation base is chosen from ortho-phenylenediamines, para phenylenediamines, double bases, ortho-aminophenols, para-aminophenols, heterocyclic bases, and the acid addition salts thereof.

13. A dyeing composition according to claim 10, wherein the couplers are chosen from meta-aminophenols, meta-phenylene-diamines, meta-diphenols, naphthols, indole derivatives, indoline derivatives, sesamol and its derivatives, pyridine derivatives, pyrazolotriazole derivatives, pyrazolones, indazoles, benzimidazoles, benzothiazoles, benzoxazoles, 1,3-benzodioxoles, quinolines, and the acid addition salts thereof.

14. A dyeing composition according to claim 10, wherein the acid addition salts of the oxidation bases and couplers are chosen from hydrochlorides, hydrobromides, sulphates, tartrates, lactates and acetates.

15. A dyeing composition according to claim 10, wherein the at least one oxidation base is present in an amount ranging from 0.0005 to 12% by weight relative to the total weight of the dyeing composition.

16. A dyeing composition according to claim 10, wherein the at least one coupler is present in an amount ranging from 0.0001 to 10% by weight, relative to the total weight of the dyeing composition.

17. A dyeing composition according to claim 1, wherein the cosmetically acceptable medium comprises at least one organic solvent.

18. A dyeing composition according to claim 17, wherein the at least one organic solvent is present in an amount ranging from 1 to 40% by weight relative to the total weight of the dyeing composition.

19. A dyeing composition according to claim 1, further comprising
   at least one cationic polymer in an amount ranging from 0.05 to 10% by weight and
   at least one nonionic surfactant in an amount ranging from 0.1 to 20% by weight relative to the total weight of the dyeing composition.

20. A method for dyeing human keratinous fibers, comprising:
   mixing at the time of use:
      a dyeing composition for the oxidation dyeing of human keratinous fibers, wherein the dyeing composition is free of oxidizing agents and comprises, in a cosmetically acceptable medium based on water and at a basic pH, at least one oxidation dye and at least one alkalinizing agent, said at least one alkalinizing agent comprising a combination of aqueous ammonia and from 1% to 3% by weight sodium metasilicate relative to the total weight of the dyeing composition, and said at least one alkalinizing agent comprising, as an active substance, at most 1.6% by weight of ammonia relative to the total weight of the dyeing composition,
      wherein the weight ratio of ammonia to sodium metasilicate is between 0.3 and 2;
      an oxidizing composition comprising an oxidizing agent chosen from hydrogen peroxide, a compound capable of releasing hydrogen peroxide in situ, and an oxidoreduction enzyme,
      wherein the weight ratio of the dyeing composition to the oxidizing composition ranges from 1.1 to 1.3;
   applying the mixture to the fibers;
   allowing the mixture to act,
   rinsing the fibers, optionally washing the fibers with shampoo and rinsing the fibers again, and
   drying the fibers.

21. The method of claim 20, wherein the human keratinous fibers are hair.

22. A ready-to-use composition for the oxidation dyeing of human keratinous fibers, comprising
   a dyeing composition for the oxidation dyeing of human keratinous fibers, wherein the dyeing composition is free of oxidizing agents and comprises, in a cosmetically acceptable medium based on water and at a basic pH, at least one oxidation dye and at least one alkalinizing agent, said at least one alkalinizing agent comprising a combination of aqueous ammonia and from 1% to 3% by weight sodium metasilicate relative to the total weight of the dyeing composition, and said at least one alkalinizing agent comprising, as an active substance, at most 1.6% by weight of ammonia relative to the total weight of the dyeing composition, wherein the weight ratio of ammonia to sodium metasilicate is between 0.3 and 2; and
   an oxidizing composition,
      wherein the weight ratio of the dyeing composition to the oxidizing ranges from 1:1 to 1:3.

23. A ready to use composition according to claim 22 wherein the human keratinous fibers are hair.

24. A ready-to-use composition according to claim 22 wherein the oxidizing composition comprises hydrogen peroxide.

25. The dyeing composition according to claim 1, wherein the at least one alkalinizing agent comprises, as an active substance, at least 0.4% by weight of ammonia relative to the total weight of the dyeing composition.

26. The method of claim 20, wherein the at least one alkalinizing agent comprises, as an active substance, at least 0.6% by weight of ammonia relative to the total weight of the dyeing composition.

27. The method of claim 20, wherein the at least one alkalinizing agent comprises, as an active substance, from 0.4% to 1.2% by weight of ammonia relative to the total weight of the dyeing composition.

28. The method of claim 20, wherein the at least one alkalinizing agent comprises, as an active substance, from 0.6% to 1% by weight of ammonia relative to the total weight of the dyeing composition.

29. The method of claim 20, wherein the at least one alkalinizing agent comprises, as an active substance, at least 0.4% by weight of ammonia relative to the total weight of the dyeing composition.

30. The ready-to-use composition according to claim 22, wherein the at least one alkalinizing agent comprises, as an active substance, at least 0.6% by weight of ammonia relative to the total weight of the dyeing composition.

31. The ready-to-use composition according to claim 22, wherein the at least one alkalinizing agent comprises, as an active substance, from 0.4% to 1.2% by weight of ammonia relative to the total weight of the dyeing composition.

32. The ready-to-use composition according to claim 22, wherein the at least one alkalinizing agent comprises, as an active substance, from 0.6% to 1% by weight of ammonia relative to the total weight of the dyeing composition.

33. The ready-to-use composition according to claim 22, wherein the at least one alkalinizing agent comprises, as an active substance, at least 0.4% by weight of ammonia relative to the total weight of the dyeing composition.

* * * * *